United States Patent [19]
Wallbridge et al.

[11] Patent Number: 5,834,058
[45] Date of Patent: Nov. 10, 1998

[54] ORGANOMETALLIC COMPLEXES OF ALUMINIUM, GALLIUM AND INDIUM

[75] Inventors: Malcolm G. H. Wallbridge, Conventry; Nicholas C. Blacker, Wiltshire; Paul R. Phillips, Berkshire; James Barker, Cheshire, all of Great Britain

[73] Assignee: The Associated Octel Company Limited, London, England

[21] Appl. No.: 591,452

[22] PCT Filed: Aug. 2, 1994

[86] PCT No.: PCT/GB94/01696

§ 371 Date: Apr. 4, 1996

§ 102(e) Date: Apr. 4, 1996

[87] PCT Pub. No.: WO95/04063

PCT Pub. Date: Feb. 9, 1995

[30] Foreign Application Priority Data

Aug. 2, 1993 [GB] United Kingdom ............. 9315975

[51] Int. Cl.$^6$ ............. C23C 14/26; C23C 8/00; C07F 5/00

[52] U.S. Cl. ............. 427/252; 556/1; 556/176; 427/585; 427/593; 427/587

[58] Field of Search ............. 556/1, 176; 427/585, 427/587, 593, 252

[56] References Cited

FOREIGN PATENT DOCUMENTS 0432574  6/1991  European Pat. Off.

OTHER PUBLICATIONS

Lechler et al., Journal of Organometallic Chemistry, vol. 359, pp. 1–12, (1989).
Hunsen et al., Journal of Organometallic Chemistry, vol. 145, pp. 277–284, (1978).
Locke et al., Journal of Organometallic Chemistry, vol. 420, pp. 1–12, (1991).

*Primary Examiner*—Porfirio Nazario-Gonzalez
*Attorney, Agent, or Firm*—Fay, Sharpe, Beall, Fagan, Minnich & McKee

[57] ABSTRACT

Novel organometallic complexes of aluminium, gallium and indium are disclosed, having improved stability and volatility for use in CVD processes. These are donor ligand complexes of the formula $MR_2L$ where M is the metal, R is an alkyl group and L is a ligand containing an amidine (R'N...C(R')...NR') group, where R' is H, alkyl etc.

16 Claims, 2 Drawing Sheets

ORGANOMETALLIC COMPLEXES OF ALUMINIUM, GALLIUM AND INDIUM

This application was filed as a request for U.S. examination under 35 U.S.C. §371 of International application No. PCT/GB94/01696 filed Aug. 2, 1994.

This invention relates to volatile organometallic complexes of aluminium, gallium and indium.

Volatile organometallic compounds of aluminium, gallium and indium, e.g. the aluminium, gallium and indium alkyls, especially trimethyl gallium and triethyl indium, are of considerable interest as volatile sources of aluminium, gallium and indium metal in CVD (chemical vapour deposition) processes. Of particular interest are CVD processes employing a volatile source of aluminium, gallium or indium in the manufacture, by chemical vapour deposition on the surface of a suitable substrate, of compound semiconductor materials such as gallium arsenide (GaAs), indium arsenide (InAs), indium phosphide (InP), indium aluminium gallium arsenide (InAlGaAs) or wide bandgap material systems such as aluminium, gallium or indium nitride.

Metal alkyls, such as trimethylaluminium, trimethylgallium and triethylindium, are, however, unstable at elevated temperature, pyrophoric and extremely sensitive to air, and are explosively hydrolytic in contact with moisture. Such materials can, therefore, be manufactured and used only under very stringent conditions.

In accordance with the present invention we have discovered that the amidine complexes of aluminium, gallium and indium dialkyls possess good stability at room temperature, are substantially non-pyrophoric, and show excellent thermal stability in the vapour phase. They are, therefore, of high utility as a volatile source of aluminium, gallium and indium in CVD processes of all kinds.

In accordance with the present invention, therefore, there are provided novel organometallic complexes of the formula I $$MR_2 \cdot L \qquad \qquad I$$

where M is aluminium, gallium or indium, R is $C_1$–$C_8$ alkyl, preferably methyl or ethyl; and L is an organic ligand containing a substituted or unsubstituted amidino [R'NC (R')NR'] group. Preferred amidine ligands are amidines of the formula II:

$$R'N(H)C(R')=NR' \qquad \qquad II$$

where R' is H, $C_1$–$C_8$ alkyl or haloalkyl, $C_3$–$C_8$ cycloalkyl, optionally including an —NH— group in the ring, $C_{3-C8}$ cycloalkenyl, phenyl or substituted phenyl containing from 1–3 ($C_1$–$C_8$)alkyl or halo-substituents, trimethylsilyl or halogen, the R' groups being the same or different.

Typical amidine ligands within that formula are N,N'-diphenylbenzamidine, N,N'-di(p-chlorophenyl)acetamidine, N,N'-diphenylformamidine, N,N'-di(p-fluorophenyl)acetamidine, benzamidine, acetamidine, and N,N'-dicyclohexylacetamidine. Other suitable amidine ligands will be apparent to those skilled in the art, as will be methods for the preparation of such amidines.

The amidine complexes of this invention are prepared by reacting a molar excess of the trialkylaluminium, trialkylgallium or trialkylindium compounds, e.g. trimethylaluminium, trimethylgallium or triethylindium with the ligand under anhydrous conditions in vacuo or under an inert atmosphere, preferably, but not necessarily in the presence of an anhydrous hydrocarbon solvent such as toluene or n-hexane. That reaction may be represented as follows:

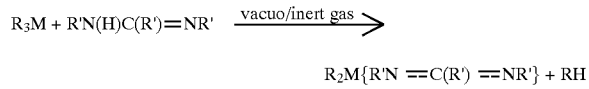

$$R_2M\{R'N=C(R')=NR'\} + RH$$

The alkane (RH) evolved during the course of the reaction is removed preferably continuously, following which the product complex can be recovered by removal of the excess aluminium, gallium or indium trialkyl and the solvent, if present, preferably by distillation in vacuo.

Whilst the alkyl substituents of the aluminium, gallium or indium trialkyl reactant will usually be the same, trialkyls containing different alkyl groups may be used giving rise to complexes of the formula I where the R groups are different.

Aluminium, gallium and indium complexes in accordance with this invention and the preparation thereof is illustrated by the following Examples and by the accompanying drawings. In all the Examples, the reactions were carried out on a vacuum line.

In the drawings

EXAMPLE 1

Dimethylgallium N,-N'-diphenylbenzamidine

N,N'-diphenylbenzamidine (0.93 g; 3.4 mmol) was placed in a round-bottomed flask with about 30 cm³ of dry toluene. A slight excess of $Me_3Ga$ was weighed out in a calibrated gas flask. The amidine solution was degassed by repeated solidification and fusion under vacuum. The $Me_3Ga$ was condensed on the amidine solution at −196° C., and the stirred mixture allowed to warm slowly to room temperature to give a yellow solution. The approximate volume of methane evolved was measured using a calibrated portion of the vacuum line, and the solvent and excess $Me_3Ga$ distilled off. The product was a slightly yellowish solid. Yield, 1.10 g (79%). Analysis, calculated for $C_{21}H_{21}N_2Ga$(M.W. 371.13): C,67.96, H,5.70:; N,7.55%. Found: C,67.85; H,5.69; N,7.46%.¹H N.M.R.(CDCl₃): $\delta_H$ 7.35–7.20(Ar—H, 5H,m), 7.08(Ar—H,4H,1, J8 Hz), 6.9 (Ar—H, 2H, t, J7 Hz), 6.63 (Ar—H, 4H, d, J8 Hz), 0.01 (Ga(CH₃)₂, 6H, s).

Figure 1:
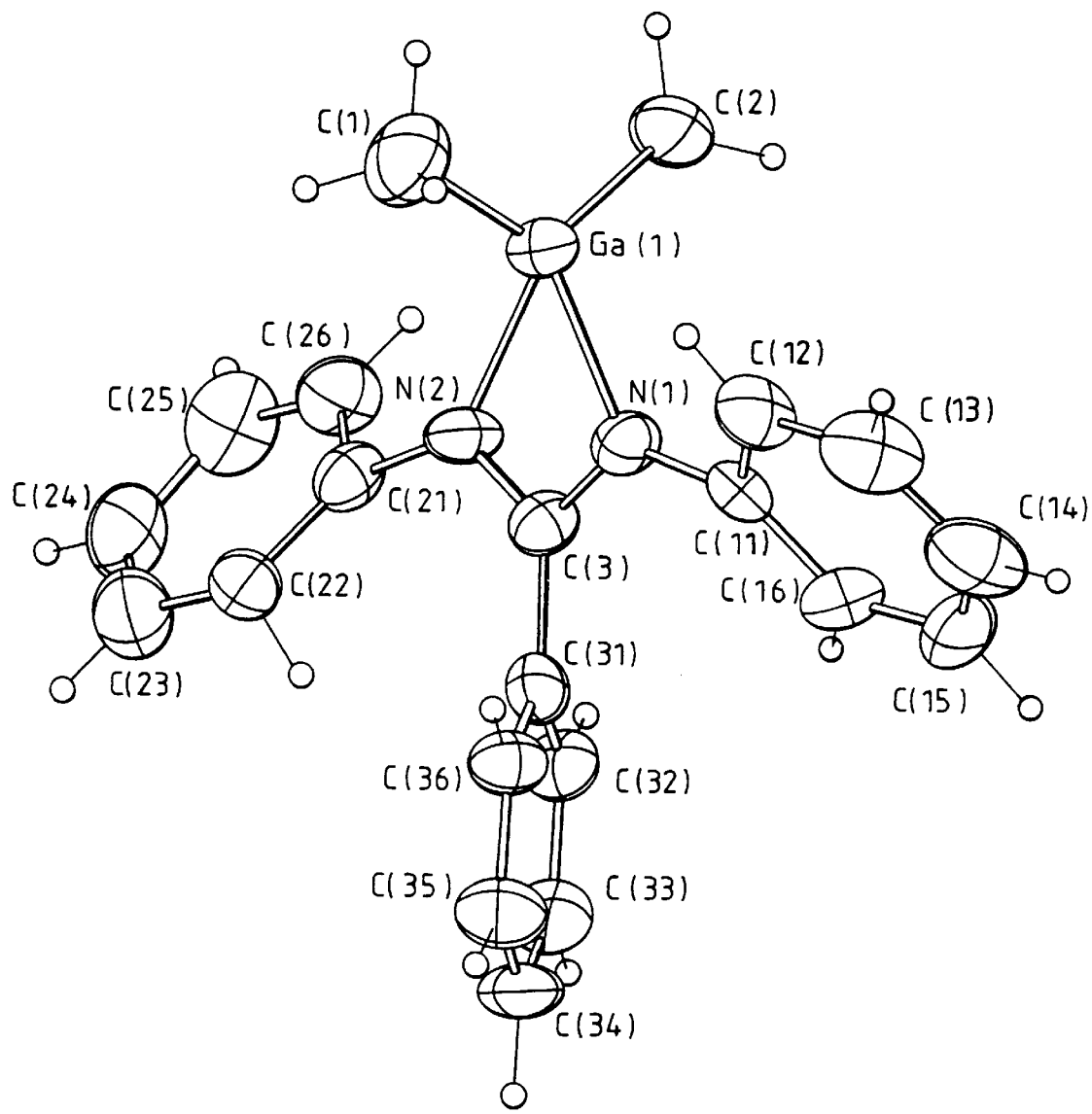
FIG. 1 shows the crystal structure of the dimethylgallium N,N'-diphenylbenzamidine complex.

Crystals of this compound suitable for X-ray diffraction were grown, and characterisation by X-Ray crystallography establishes the structure of the complex to be monomeric and as shown in FIG. 1 of the accompanying drawings.

The complex sublimes rapidly at 90° C. and 0.03 mmHg with 36% sublimate formation after 20 minutes. Melting points (in sealed tubes) starting complex 102.5°–103° C.; sublimate 96.5°–97.0° C.; residue 96.0° to 97.0° C.

EXAMPLE 2

Dimethylgallium N,N'-di(p-chlorophenyl) acetamidine

The process used was the same as that used for the N,N'-diphenylbenzamidine complex, Example 1, but using N,N'-di(p-chlorophenyl)acetamidine in place of N,N'-diphenylbenzamidine. The product is a white solid which sublimes fairly rapidly at 120° C. under vacuum. This and other acetamidine complexes were found to crystallise as small needles. Yield, 0.99 g (63%). Analysis, calculated for $C_{16}H_{17}N_2Cl_2Ga$ (M.W. 377.95): C, 50.85; H, 4.53; N, 7.41%. Found: C, 50.74; H, 4.41; N, 7.28%, $^1$H.N.M.R. ($C_6D_5CD_3$): $\delta_H$ 7.12, (Ar—H, 4H,d), 6.61 (Ar—H,4H,d), 1.42 ($CH_3$,3H,s) −0.11–0.15 ($Ga(CH_3)_2$, 6H, s).

EXAMPLE 3

Dimethylgallium N,N'-diphenylformamidine

Before use the amidine, N,N'-diphenylformamidine, was recrystallised from methanol to give pale pink needles and dried under vacuum. The procedure of Example 1 was repeated, using N,N'-diphenylformamidine in place of N,N'-diphenylbenzamidine and n-hexane in place of toluene. The product was recovered as a crystalline mass. Yield:, 0.97 g (75%). Analysis, calculated for $C_{15}H_{17}N_2Ga$ (M.W. 295.03). C, 61.07; H, 5.81; N, 9.50%. Found: C, 59.25; H, 5.83; N, 9.26%. $^1$H N.M.R. ($CDCl_3$): $\delta_H$ 8.75 (C—H,1H,s) 7.30 (Ar—H, 4H,t,J 8 Hz) 7.07–6.96 (Ar—H,6H,m) 0.15 (Ga($CH_3$)$_2$, 6H, s).

EXAMPLE 4

Dimethylgallium N,N'-diphenylacetamidine

Using n-hexane as the solvent, the complex was prepared as in Example 1. The product is a white solid. Yield, 1.08 g. (71%). Analysis, calculated for $C_{16}H_{19}N_2Ga$ (M.W. 309.18): C, 62.20; H, 6.20; N, 9.06%. Found: C, 62.55; H, 6.05; N, 8.87%. 1H NMR ($CDCl_3$) 7.35 (Ar—H, 4H, t, J 8 Hz) 7.10 (Ar—H, 2H, t, J 7 Hz) 7.01 (Ar—H, 4H, d, J 8 Hz) 2.20 ($CH_3$ 1H, s) 0.03 ($Ga(CH_3)_2$ 6H, s)

EXAMPLE 5

Dimethylgallium N,N'-di(p-tolyl)benzamidine

Using n-hexane as the solvent, the procedure of Example 1 was used to prepare the di(p-tolyl)benzamidine complex. The product is a pale yellow solid. Yield, 1.10 g (74%). Analysis, calculated for $C_{23}H_{25}N_2Ga$. (M.W. 399.18): C, 69.20; H, 6.31; N, 7.02%. Found: C, 69.87; H, 6.29; N, 7.07%. 1H NMR ($CDCl_3$) $\delta_H$ 7.35 (Ar—H,5H,m) 6.95 (Ar—H,4H,d) 6.60 (Ar—H,4H,d) −0.28–0.00 ($Ga(CH_3)_2$, 6H, s).

EXAMPLE 6

Dimethylgallium N,N'-di(p-tolyl)acetamidine

Using n-hexane as the solvent the procedure of Example 1 was used to prepare the N,N'-di(tolyl)acetamidine complex. The product is a white solid. Yield, 0.56 g (88%). Analysis, calculated for $C_{18}H_{23}N_2Ga$ (M.W. 337.11): C, 64.13; H, 6.88; N, 8.31%. Found: C, 65.56; H, 6.82; N, 8.87%. 1H N.M.R. ($CDCl_3$) $\delta_H$ 7.15 (Ar—H, 4H, d) 6.93 (Ar—H, 4H, d) 2.33 ($CH_3$, 6H, s) 2.10 ($CH_3$3H,s) −0.50–0.08 (Ga(CH $_3$)$_2$, 6H, s).

EXAMPLE 7

Dimethylgallium N,N'-di(p-fluorophenyl) acetamidine

Using n-hexane as the solvent, the procedure of Example 1 was used to prepare the N,N'-di(p-fluorophenyl)acetamidine complex. The product is a colourless crystalline solid. Yield, 1.8 g (89%). Analysis, calculated for $C_{16}H_{17}N_2GaF_2$ (M.W. 345.04): C, 55.70; H, 4.97; N, 8.12%. Found: C, 55.77; H, 4.86; N, 7.96%. 1H N.M.R. ($CDCl_3$) $\delta_H$ 7.10–6.90 (Ar—H, 10H, m) 2.07 ($CH_3$ 3H, s) −0.45–0.04 ($Ga(CH_3)_2$, 6H, s)

EXAMPLE 8

Dimethylindium N,N'-diphenylbenzamidine

To a suspension of N,N'-diphenylbenzamidine (0.80 g, 2.94 mmol) in hexane (40 cm$^3$) $In(CH_3)_3$ (10% excess) was added under an argon atmosphere at −196° C. The mixture was allowed to warm to room temperature and stirred for 2 hours. The resulting light green solution was reduced in volume to ca. 25 cm$^3$. and a pale yellow solid precipitated. The suspension was held at −35° C. for 24 hours and the solid isolated via filtration, washed with hexane (2×10 cm$^3$.) and pumped dry for 3 hours. Yield: 0.88 g (65%). Analysis, calculated for $C_{21}H_{21}N_2In$(M.W. 416.23): C,60.60, H=6.73; N=5.09%. Found C,58.06, H,6.38; N=5.09%. 1H N.M.R. ($C_6D_5CD_3$), $\delta_H$ 7.09–6.65 (Ar—H, 15H, m) 0.189 ($In(CH_3)_2$, 6H, s)

The crystallographic structure of the complex is similar to that shown in FIG. 1, with indium replacing gallium.

EXAMPLE 9

Dimethylgallium N,N'-dicyclohexylacetamidine

In an initial reaction N,N'-dicyclohexylacetamidine was prepared by the reaction of dicyclohexylcarbodiimide with methyl lithium. For this purpose dicyclohexylcarbodiimide (2.65 g, 12.85 mmole) was dissolved in 50 cm$^3$ diethylether (10 cm$^3$, 15 mmol). The reaction mixture was left stirring for about two hours before distilled water (10 cm$^3$) was added cautiously. The ether layer was washed with a further 10 cm$^3$ of water. After separating, the ether was removed under vacuum to give an oil. This was redissolved in ether (2 cm$^3$) and the solution transferred to a sublimer. The ether was removed again at room temperature and the oil heated. A white solid sublimes rapidly at 100° C. Yield, 2.06 g (72%). Analysis, calculated for $C_{14}H_{26}N_2$ (M.W. 222.38): C, 75.62; H, 11.79; N, 12.60%. Found: C, 75.70; H, 11.63; N, 11.82%. 1H N.M.R. ($CDCl_3$) $\delta_H$ 3.10–3.45 (CH, 1H, m) 2.75–2.95 (CH, 1H, m),1.20–1.95, 1.77, 1.96 ($CH_2$+$CH_3$. 23H, m).

Trimethylgallium was condensed directly onto the solid amidine at −196° C. in the absence of any solvent. The reaction mixture liquified then set solid. Yield, 10.7 g (95%). Analysis, calculated for $C_{16}H_{31}N_2Ga$ (M.W. 321.15): C, 59.84; H, 9.73; N, 8.72%. Found: C, 61.35; H, 9.66; N, 8.95%. 1H N.M.R. ($CDCl_3$) $\delta_H$ 3.05–3.25 (CH, 2H, m) 1.87 ($CH_3$, 3H, s,) 1.80–0.95 ($CH_2$, 20H, m,)0.31 ($Ga(CH_3)_2$, 6H, s).

EXAMPLE 10

Dimethylgallium benzamidine

Benzamidine was first prepared by dissolving 1.42 g (62 mmole) sodium in methanol, and adding 9.65 g (61 mmole) benzamidine hydrochloride hydrate. This was left to stir for one hour before the solvent was removed under vacuum and a cold finger inserted. Benzamidine sublimed fairly quickly at 80° C. Yield, 5.20 g (70%). The amidine was re-sublimed before use. N.M.R. ($CDCl_3$) $\delta_H$ 7.35 (3H, s, NH, $CHCl_3$, 7.50 (3H, m, $C_6H_5$), 7.68 (2H, m, $C_6H_5$). The singlet at 7.35 p.p.m. is probably due to proton deuterium exchange between $CDCl_3$ and the amidine.

The amidine was then reacted with trimethylgallium in the absence of solvent, to give a foamy solid. Yield, 0.42 g (58%). Analysis, calculated for $C_9H_{13}N_2Ga$ (M.W. 218.94): C, 49.371; H, 5.98; N, 12.80%. Found: C, 49.63; H, 6.00; N, 12.11%. 1H N.M.R. $(C_6D_5CD_3)$ $\delta_H$ 7.35 (Ar—H, 2H, m) 7.10 (Ar—H, 3H, m) 4.63 (N—H,1H,br.s)–0.27 $(Ga(CH_3)_2$ 6H, s).

EXAMPLE 11

Dimethylgallium acetamidine

Acetamidine was prepared by heating the hydrochloride salt (2.77 g, 29 mmole) with potassium hydroxide (approximately 8 g, 140 mmoles) at 120° C. under vacuum so the amidine sublimes out of the reaction mixture. Yield, 1.32 g (78%). The white solid was re-sublimed under vacuum at about 50° C. before use. Analysis, calculated for $C_2H_6N_2$ (M.W. 58.08): C, 41.36; H, 10.41; N, 48.28%. Found: C, 41.95; H, 10.17; N, 47.30%. 1H N.M.R. $(CDCl_3)$ $\delta_H$ 1.98 (3H, s, $CH_3$), 7.36 (3H, s, $NH/CHCl_3$).

Using n-hexane as the solvent and following the procedure of Example 1, the acetamidine was reacted with trimethylgallium to produce the dimethylgallium-acetamidine complex. The product is a white solid. Yield, 0.45 g (57%). Analysis, calculated for $C_4H_{11}N_2Ga$ (M.W. 156.87): C, 30.63; H, 7.07; N, 17.86%. Found: C, 31.53; H, 7.36; N, 16.25%. 1H N.M.R. $(CDCl_3)$ $\delta_H$ 7.34 (NH, 2H, s)1.99 ($CH_3$ 3H, s)–0.46 $(Ga(CH_3)_2$, 6H s).

EXAMPLE 12

Diethylindium N,N'-diphenylbenzamidine

Preparation as in Example 8. Pale yellow solid isolated. Yield 1.05 g. (70%). 1H N.M.R. $(CDCl_3)$ 7.24–7.12 (Ar—H, 5H, m), 7.07 (Ar—H, 4H, t, J 8 Hz) 6.85 (Ar—H, 2H, t, J 6 Hz) 6.63 (Ar—H, 4H, d, J4 Hz) 1.45 $(In(CH_2\underline{CH_3})_2$. 6H, t, J 8 Hz) 0.98 $(In\underline{CH_2}CH_3)_2$, 4H, q, J9 Hz.

The complex sublimes at 107° C. and 0.03 mmHg with 31% sublimate formation after 1–5 hours. Melting points (in sealed tubes) starting complex 101.5°–102.5° C.; sublimate 102°–103.5° C.

EXAMPLE 13

Diethylindium N,N'-di(p-chlorophenyl)benzamidine

Preparation as in example 8. Product is a green solid. Yield 0.86 g (78%). 1H NMR $(CDCl_3)$ 7.32–7.18 (Ar—H, 3H, m) 7.11 (Ar—H, 2H, d,d, J8 Hz, 2 Hz)7.01 (Ar—H, 4H, d, t, J8 Hz, 3 Hz) 6.52 (Ar—H, 4H, d, t, J 8.5 Hz, 2 Hz) 1.41 $(In(CH_2\underline{CH_3})_2$ 0.98 $(In\underline{CH_2}CH_3)_2$.

The crystallographic structure is similar to that shown in FIG. 1, with ethyl replacing methyl and N,N'-di(p-chlorophenyl)benzamidine replacing the N,N'-diphenylbenzamidine.

EXAMPLE 14

Diethylgallium N,N'-diphenylbenzamidine

Preparation as in example one. Yellow crystals/solid isolated from hexane. Yield 0.69 (68%). 1H NMR $(CDCl_3)$ 7.40–7.25 (Ar—H, 5H, m) 7.12 (Ar—H, 4H, t, J 7 Hz) 6.93 (Ar—H, 2H, t, J 7 Hz) .6.67 (Ar—H, 4H, d, J 9 Hz) 1.26 $(Ga(CH_2CH_3)_2$, 6H, t, J 8 Hz) 0.76 $(Ga(CH_2CH_3)_2$ 4H, q, J 8 Hz.

EXAMPLE 15

Dimethylgallium N,N'-di(p-chlorophenyl) benzamidine

Preparation. To a suspension of N'N-di(p-chlorodiphenyl) benzamidine (0.95 g. 2.79 mmol) in hexane (40 cm³) was distilled under vacuum $Ga(CH_3)_3$ (10% excess). On warming to room temperature and stirring for 3 hours a yellow solution and solid was obtained. The solvent was removed under vacuum leaving a yellow solid. Yield 0.99 g. (78%). Analysis, calculated for $C_{21}H_{19}N_2Cl_2Ga$. (M.W. 440.42): C,57,32; G,4.35; N,6.37%. Found: C,57.66; H,4.63; N,6.05%. 1H NMR $(CDCl_3)$ 7.38 (Ar—H, 1H, t, J 7 Hz) 7.29 (Ar—H, 2H, t, J 7 Hz), 7.19 (Ar-h, 2H, d, J 8 Hz), 7.03 (Ar—H, 4H, d, J 7 Hz), 6.54(Ar—H, 4H, d, J 8 Hz) –0.01 $(Ga(CH_3)_2$. 6H, s)

EXAMPLE 16

Dimethylgallium N,N'-di(3,4-dichlorophenyl) formamidine

Preparation as in Example 15, but using NmN'-di(3,4-dichlorophenyl) formamidine in place of N,N'-di (p.chlorophenyl)benzamidine. Yield 0.74 g. (74%). Analysis, calculated for $C_{13}H_{13}N_2Cl_4Ga$(M.W.432.81): C,41.63; H, 3.03; N,6.47%. Found: C,41.79; H,3.18; N,6.15%. 1H NMR $(CDCl_3)$ 8.60 (c-H, 1H, s), 7.32 (Ar—H, 2H, d, J 8 Hz) 7.05 (Ar—H, 2H,d, J 2.5 Hz) 6.80 (Ar—H, 2H, d, d, j 9 Hz), J 2.5 Hz) 0.034 $(Ga(CH_3)_2$, 6H, s)

EXAMPLE 17

Dimethylaluminium N,N'-diphenylbenzamidine

Preparation. To a suspension of N,N'-diphenylbenzamidine (0.95 g. 3.12 mmol) in hexane (40 cm³) was added a solution of $Al(CH_3)_3$ in hexane (2.0M) via syringe in 15% excess at –196° C. The mixture was allowed to warm to room temperature with stirring for 2 hours. The resulting pale green solution was reduced in volume under vacuum to ca. 25 cm³. and placed at –35° C. for 24 hours giving a pale green solid, isolated via filtration and washed with hexane (2×10 cm³) . Yield $0.6^6$ g. (64%). Analysis, calculated for $C_{21}H_{21}N_2Al$. (M.W.328.39): C, 76.81;H, 6.45; N,8.53%. Found: C, 75.21; H, 6.13; N, 8.30%. 1H NMR $(CDCl_3)$ 7.34 (Ar—H, iH, t, J, 7 Hz) 7.31–7.18(Ar—H, 4H, m) 7.11 (Ar—H,4H, t, J 6 Hz) 6.96 (Ar—H, 2H, t, J 7 Hz) 6.68 (Ar—H, 4H, d, J 8 Hz) –0.51 $(Al(CH_3)_2$, 6H, s).

The complex sublimes rapidly at 103° C. and 0.03 mmHg with 42% sublimate formation after 1 hour. Melting points (in sealed tubes) starting complex 108°–109° C.; sublimate 110°–110.5° C.; residue 109.5°–110° C.

EXAMPLE 18

Dimethylaluminium N,N'-diphenylacetamidine

Preparation as Example 17. The product is a white solid. Yield 0.84 g. (70%). Analysis, calculated for $C_{16}H_{19}N_2Al$. (M.W. 266.32): C,72.16; H, 7.19; N, 10.50%. Found: C,71.41; H, 7.16; N,10.46%. $^1$—H NMR $(CDCL_3)$ 7.35 (Ar—H, 4H, t, J 8 Hz) 7.12 (Ar—H, 2H, t, J 7.5 Hz) 7.02 (Ar—H, 4H, d, J 8 Hz) 2.21 ($CH_3$ 3H,s)–0.54 $(Al(CH_3)_2$, 6H, s).

EXAMPLE 19

Dimethylaluminium N,N'-diphenylformamidine

Preparation as in Example 17. Product is a white solid. Yield 0.71 g. (68%). Analysis, calculated for $C_{15}H_{17}N_2Al$ (M.W.300–34): C,71.41; H, 6.79; N, 11.10%. Found: C.70.82; H, 6.79; N,10.77%. $^1$H NMR $(CDCl_3)$ 7.36 (Ar—H, 1H, s) 6.75–6.68 (Ar—H, 6H, m) 6.23 (Ar—H, 4H, d, J 8 Hz) –1.02 $(Al(CH_3)_2$, 6H, s)

EXAMPLE 20

Dimethylaluminium N,N'-di(p-chlorophenyl) benzamidine

Preparation as in Example 16. Product is a pale green/yellow solid. Yield 0.71 g. (68%). Analysis, $^1$H NMR (CDCl$_3$) 7.42(Ar—H, 1H, t, 7 Hz) 7.31 (Ar—H, 2H, t, J 8 Hz) 7.17 (Ar—H, 2H, d, J 7 Hz) 7.07(ArH, 4H, d, J 9 Hz), 6.59(Ar-h, 4H,d, J 9 Hz), −0.53 (Al(CH$_3$)$_2$, 6H, s).

EXAMPLE 21

Dimethylaluminium N,N'-di(p-chlorophenyl) acetamidine

Preparation as in Example 17. Product is a white solid. Yield 0.49 g. (65%). Analysis, calculated for C$_{16}$H$_{17}$N$_2$Cl$_2$Al.(M.W. 335.21): C, 57.33; H, 5.11, N, 8.36%. Found: C, 56.75%H=5.18;N,8.34%. $^1$H NMR (CDCl$_3$) 7.29 (Ar—H, 4H, d, J 8 Hz) 6.92 (Ar—H, 4H, d, J 8 Hz) 2.16 (CH$_3$, 3H, s)–0.56 (Al(CH$_3$)$_2$, 6H, s).

Figure 2:
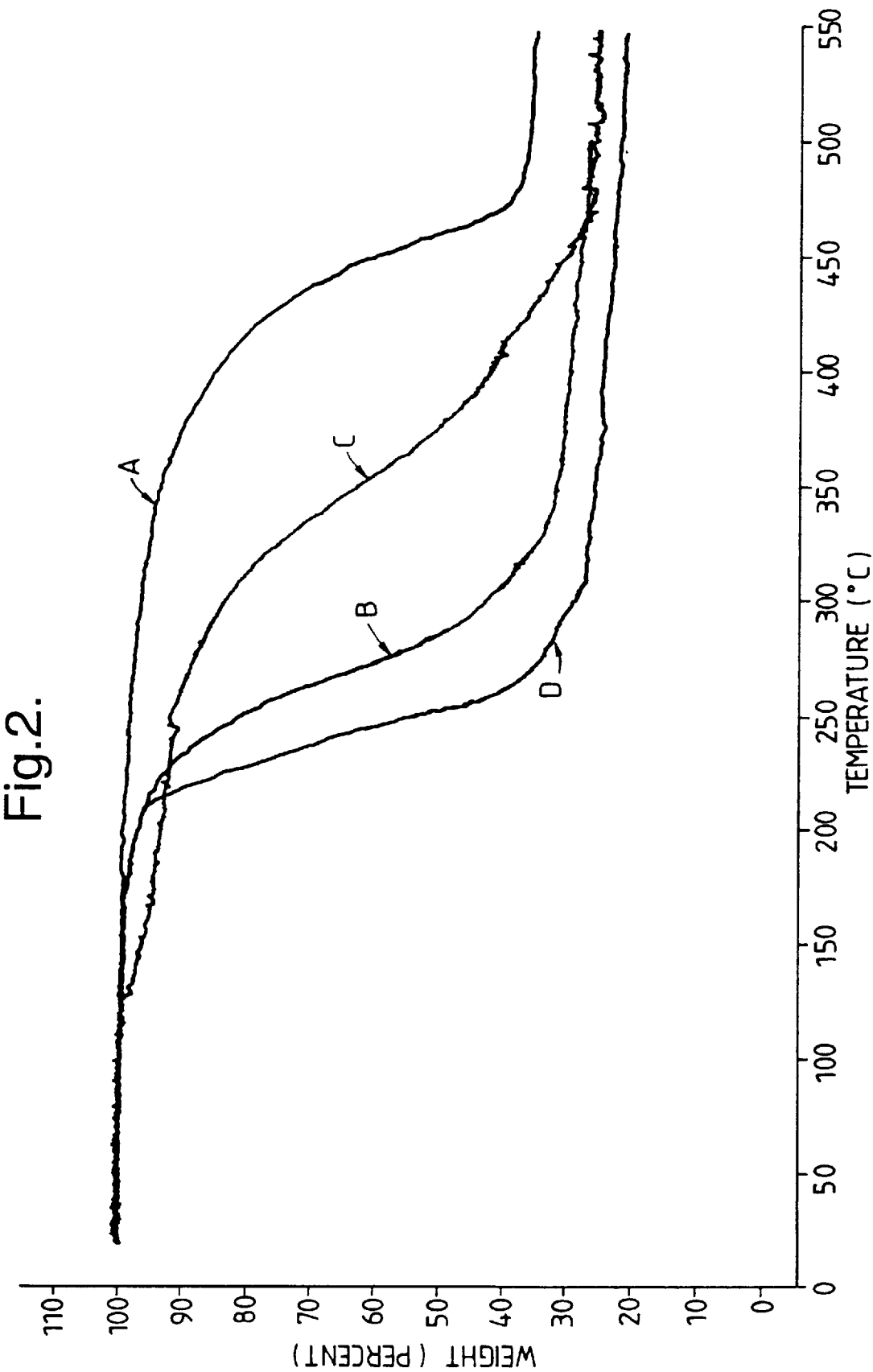
FIG. 2 shows the thermogravimetric analysis curve of that and various other complexes according to the invention.

The (TGA) thermogravimetric analysis curves of various complexes according to the present invention are presented in FIG. 2 and show the complexes to be thermally stable to at least 110° C., (e.g. curve C), allowing ease of handling at ambient and moderately elevated temperatures, The curves also show the materials lose the ligand in a single clean step at a higher temperatures. The following key applies
Curve A Me$_2$In N,N'-diphenylbenzamidine (Example 8)
Curve B Me$_2$Ga N,N'-diphenylbenzamidine (Example 1)
Curve C Me$_2$ Al N,N'-diphenylbenzamidine (Example 17)
Curve D Me$_2$ Ga N,N'-di(3,4-dichlorophenyl)formamidine (Example 16)

In Examples 1, 2, 12 and 17, the volatility of the complexes has been demonstrated by their sublimation intact under relatively mild vacuum, the intact nature of the sublimate being demonstrated by its characteristic melting point (sealed tube), and the residue melting-point. Any slight difference may be attributed to concentration of impurities in the residue which is a useful characteristic. Thus the complexes may be readily volatilised intact, and have a useful thermal stability range; both of which properties make them useful metal precursors in metal CVD operations.

Further, observation of parent ions in the mass-spectra of these complexes may be thought indicative of the thermal-stability-volatility of such complexes under vacuo and thermal load.

We claim:

1. Organometallic aluminum, gallium and indium complexes of the formula I:

$$MR_2.L \qquad \qquad I$$

where M is aluminum, gallium or indium;
R is C$_1$–C$_8$ alkyl, the two R groups being the same or different, and
L is an amidino group of the formula II

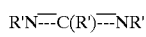   II derived from any of the following:
acetamidine
benzamidine
N,N'-diphenylbenzamidine
N,N'-di(p-chlorophenyl) acetamidine
N,N'-diphenylformamidine
N,N'-diphenylacetamidine
N,N'-di(p-tolyl)benzamidine
N,N'-di(p-fluorophenyl) acetamidine
N,N'-dicyclohexylacetamidine
and where R'is H, C$_1$–C$_8$ alkyl or haloalkyl, C$_3$–C$_8$ cycloalkyl optionally including an NH-group in the ring, C$_3$–C$_8$ cycloalkyl, phenyl, substituted phenyl containing from 1–3 (C$_1$–C$_8$) alkyl or halo-substituents, trimethylsilyl or halogen, the R' groups being the same or different.

2. Organometallic aluminium, gallium and indium complexes according to claim 1, where R is methyl or ethyl.

3. Organometallic aluminum, gallium and indium complexes according to claim 1, where in the formula I, the R groups are the same.

4. A method for the chemical vapour phase deposition of aluminium, gallium, or indium on a substrate which comprises contacting the substrate with a volatile organometallic gallium or indium in the vapour phase, wherein there is used an organometallic aluminium, gallium or indium complex according to claim 1.

5. Organometallic aluminum, gallium and indium complexes according to claim 2, where in the formula I, the R groups are the same.

6. A method for the chemical vapour phase deposition of aluminium, gallium, or indium on a substrate which comprises contacting the substrate with a volatile organometallic gallium or indium in the vapour phase, wherein there is used an organometallic aluminium, gallium or indium complex according to claim 2.

7. A method for the chemical vapour phase deposition of aluminium, gallium, or indium on a substrate which comprises contacting the substrate with a volatile organometallic gallium or indium in the vapour phase, wherein there is used an organometallic aluminium, gallium or indium complex according to claim 3.

8. A method for the chemical vapour phase deposition of aluminum, gallium or indium on a substrate which comprises contacting the substrate with a volatile organometallic gallium or indium in the vapour phase, wherein there is used an organometallic aluminum, gallium or indium complex; wherein the organometallic aluminum, gallium or indium complex is of the formula I:

$$MR_2.L \qquad \qquad I$$

where M is aluminum, gallium or indium,
R is C$_1$–C$_8$ alkyl, the two R groups being the same or different, and
L is an amidino group of the formula II

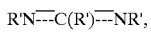,   II where R' is H, C$_1$–C$_8$ alkyl or haloalkyl, C$_{3-C8}$ cycloalkyl optionally including an NH-group in the ring, C$_{3-C8}$ cycloalkyl, phenyl, substituted phenyl containing from 1–3 (C$_1$–C$_5$) alkyl or halo-substituents, trimethylsilyl or halogen, the R' groups being the same or different.

9. A method according to claim 8 wherein R is methyl or ethyl.

10. A method according to claim 8 wherein the R groups are the same.

11. A method according to claim 9 wherein the R groups are the same.

12. A method according to claim 8 wherein the amidine group is derived from any one of the following:
acetamidine
benzamidine N,N'-diphenylbenzamidine
N,N'-di(p-chlorophenyl) acetamidine
N,N'-diphenylformamidine
N,N'-diphenylacetamidine
N,N'-di(p-tolyl)benzamidine
N,N'-di(p-fluorophenyl) acetamidine
N,N'-dicyclohexylacetamidine.

13. Organometallic aluminum, gallium and indium complexes of the formula I:

$$MR_2 \cdot L \qquad \qquad I$$

where M is aluminum, gallium or indium;
R is $C_1-C_8$ alkyl, the two R groups being the same or different, and
L is an amidino group of the formula II $$R'N\overline{=}C(R')\overline{=}NR' \qquad \qquad II$$

where R' is H, $C_1-C_8$ alkyl or haloalkyl, $C_3-C_8$ cycloalkyl optionally including an NH-group in the ring, $C_3-C_8$ cycloalkyl, phenyl, substituted phenyl containing from 1–3 ($C_1-C_5$) alkyl or halo-substituents, trimethylsilyl or halogen, the R' groups being the same or different, and wherein the amidino group is neither $(NSi\ Me_3)_2Cme$ nor $(NMe)_2Cme$.

14. Organometallic aluminum, gallium and indium complex according to claim 13 wherein R is methyl or ethyl.

15. Organometallic aluminum, gallium and indium complex according to claim 13 wherein the R groups are the same.

16. Organometallic aluminum, gallium and indium complex according to claim 13 wherein the amidine group is derived from any of the following:
acetamidine
benzamidine
N,N'-diphenylbenzamidine
N,N'-di(p-chlorophenyl) acetamidine
N,N'-diphenylformamidine
N,N'-diphenylacetamidine
N,N'-di(p-tolyl)benzamidine
N,N'-di(p-fluorophenyl) acetamidine
N,N'-dicyclohexylacetamidine.

* * * * *